United States Patent
Bal et al.

(10) Patent No.: US 9,730,664 B2
(45) Date of Patent: Aug. 15, 2017

(54) MULTI-BED ELASTIC MOTION CORRECTION

(71) Applicant: Siemens Medical Solutions USA, Inc., Malvern, PA (US)

(72) Inventors: Girish Bal, Knoxville, TN (US); Matthias Fenchel, Erlangen (DE); William Curtis Howe, Knoxville, TN (US); Frank Kehren, Knoxville, TN (US)

(*) Notice: Subject to any disclaimer, the term of this patent is extended or adjusted under 35 U.S.C. 154(b) by 228 days.

(21) Appl. No.: 14/672,464

(22) Filed: Mar. 30, 2015

(65) Prior Publication Data

US 2015/0289832 A1   Oct. 15, 2015

Related U.S. Application Data

(60) Provisional application No. 61/979,133, filed on Apr. 14, 2014.

(51) Int. Cl.

| G06K 9/00 | (2006.01) |
|---|---|
| A61B 6/00 | (2006.01) |
| A61B 6/03 | (2006.01) |
| A61B 5/00 | (2006.01) |
| G01R 33/48 | (2006.01) |
| A61B 5/055 | (2006.01) |

(52) U.S. Cl.
CPC ............ *A61B 6/5264* (2013.01); *A61B 6/032* (2013.01); *A61B 6/037* (2013.01); *A61B 6/4417* (2013.01); *A61B 5/0035* (2013.01); *A61B 5/055* (2013.01); *A61B 6/5205* (2013.01); *A61B 6/5247* (2013.01); *A61B 6/5288* (2013.01); *G01R 33/481* (2013.01)

(58) Field of Classification Search
CPC ....... A61B 6/5264; A61B 6/032; A61B 6/037; A61B 6/4417; A61B 5/055; A61B 5/0035; A61B 6/5247; A61B 6/5288; A61B 6/5205; G01R 33/481
USPC .......................... 600/407–480; 382/128–132
See application file for complete search history.

(56) References Cited

U.S. PATENT DOCUMENTS

| 8,472,683 B2* | 6/2013 | Manjeshwar | A61B 6/032 |
|---|---|---|---|
| | | | 382/128 |
| 8,938,280 B2* | 1/2015 | Harvey | G01R 33/481 |
| | | | 600/407 |

(Continued)

OTHER PUBLICATIONS

Hong, I.; Burbar, Z.; Michel, C. "Comparisons motion correction methods for PET studies "IEEE Nuclear Science Symposium and Medical Imaging Conference Record (NSS/MIC), 2012, p. 3293-3294.

(Continued)

*Primary Examiner* — Sanjay Cattungal

(57) ABSTRACT

A set of first modality data (e.g., MR or CT) is provided. The set of first modality data comprises a plurality of mu-maps, a plurality of motion vectors and a plurality of gated data. Each of the mu-maps corresponds to one of the beds. A set of second modality data (e.g., PET/SPECT) is provided. The set of second modality data comprises a plurality of frames for each of the beds. Each of the plurality of frames is warped by one or more motion vectors of the plurality of motion vectors. A single-bed image is generated for each bed by summing the frames corresponding to the bed. A whole body image is generated by summing the single-bed images for each of the beds.

17 Claims, 10 Drawing Sheets

(56) References Cited

U.S. PATENT DOCUMENTS

| | | |
|---|---|---|
| 2012/0281897 A1 | 11/2012 | Razifar et al. |
| 2014/0200848 A1 | 7/2014 | Panin et al. |
| 2014/0355855 A1 | 12/2014 | Miao et al. |
| 2015/0065854 A1* | 3/2015 | Ahn .................... A61B 6/5247 600/411 |

OTHER PUBLICATIONS

I.K. Hong, J. Jones, M. Casey "Elastic Motion Correction for Cardiac PET Studies" IEEE-MIC M10-6 2013.

M. Dawood, F. Büther, X. Jiang, and K.P. Schäfers, "Respiratory Motion Correction in 3-D PET Data With Advanced Optical Flow Algorithms", IEEE TMI, vol. 27, No. 8, Aug. 2008.

F. Gigengack, L. Ruthotto, M. Burger, C. H. Wolters, X. Jiang, and K. P. Schäfers, "Motion Correction in Dual Gated Cardiac PET Using Mass-Preserving Image Registration", IEEE TMI, vol. 31, No. 3, Mar. 2012.

C. Chefd'hotel, G. Hermosillo, O. Faugera, "Flows of Diffeomorphisms for Multimodal Image Registration", IEEE 2002.

S.Y. Chun, and J.A. Fessler, "Spatial Resolution Properties of Motion-Compensated Tomographic Image Reconstruction Methods", IEEE TMI, vol. 31, No. 7, Jul. 2012.

J.J. Hamill, G. Bosmans, A. Dekker. Respiratory gated CT as a tool for the simulation of breathing artifacts in PET and PET/CT. Med Phys. Feb.;35(2):576-85. 2008.

R. Grimm, S. Fürst, et al., "MR-PET Respiration Compensation Using Self-Gated Motion Modeling," Proc. Intl. Soc. Mag. Reson. Med. 21, 829, 2013.

P.J. Schleyer, M.J. O'Doherty, S.F. Barrington, and P.K. Marsden. "Retrospective data-driven respiratory gating for PET/CT," Physics in medicine and biology, 54(7):1935-50, Apr. 2009.

M. Dawood, F. Gigengack, X. Jiang, K.P. Schäfers, "A mass conservation-based optical flow method for cardiac motion correction in 3D-PET." Med. Phys. (40) Jan. 25, 2005, Jan. 2013.

A. Martinez-Möller, M. Souvatzoglou, G. Delso, R. Bundschuh, C. Chefd'hotel, S. I. Ziegler, N. Navab, M. Schwaiger, S. Nekolla, "Tissue Classification as a Potential Approach for Attenuation Correction in Whole-Body PET/MRI: Evaluation with PET/CT Data". Journal of Nuclear Medicine 2009;50:520-526.

R. Grimm, S. Füst, Dregely, Forman, Hutter, S.I. Ziegler, S. Nekolla, Kiefer, M. Schwaiger, Hornegger, Block: "Self-gated Radial MRI for Respiratory Motion Compensation on Hybrid PET/MR Systems", MICCAI Proceedings 2013.

W.P. Segars, G. Sturgeon, S. Mendonca, J. Grimes, and B.M.W. Tsui, "4D XCAT phantom for multimodality imaging research." Med Phys, vol. 37, No. 9, p. 4902:15, 2010.

M. Fieseler et al., "A dynamic thorax phantom for the assessment of cardiac and respiratory motion correction in PET/MRI: A preliminary evaluation" Nuclear Instruments and Methods in Physics Research A 702 (2013) 59-63.

I. Polycarpou et al., "Impact of respiratory motion correction and spatial resolution on lesion detection in PET: a simulation study based on real MR dynamic data" Phys. Med. Biol. 59 (2014) 697-713.

S. Lingala et al., "Unified Reconstruction and Motion Estimation in Cardiac Perfusion MRI," IEEE ISBI, Chicago, Apr. 2011, pp. 65-68.

\* cited by examiner

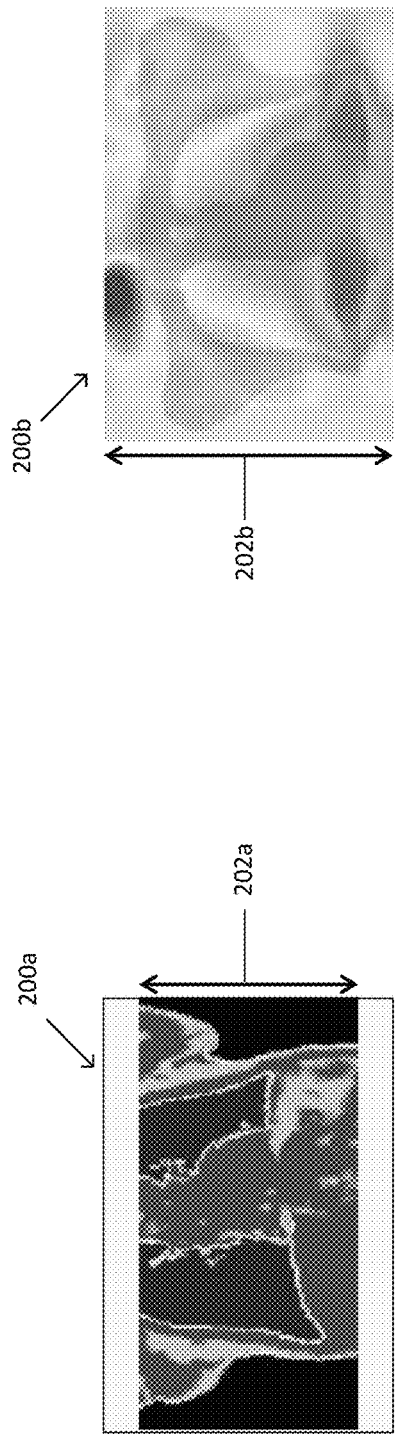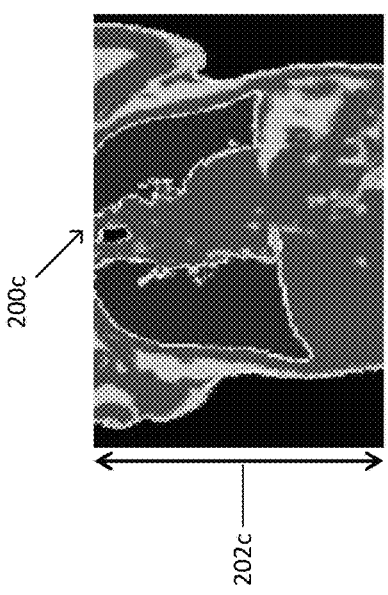
FIG. 2B
FIG. 2C
FIG. 2A

MULTI-BED ELASTIC MOTION CORRECTION

CROSS-REFERENCE TO RELATED APPLICATION

This application claims priority under 35 U.S.C. §119(e) to U.S. Provisional Application Ser. No. 61/979,133 filed Apr. 14, 2014, the entirety of which is incorporated by reference herein.

FIELD

Aspects of the present disclosure relate in general to processing data for medical imaging, and more particularly to techniques for motion correct in multi-bed medical image processing and generation.

BACKGROUND

Multi-modality imaging systems perform diagnostic scans using multiple modalities, such as, for example, magnetic resonance (MR/MRI), computed tomography (CT), positron emission tomography (PET), and/or single photon emission computed tomography (SPECT). Multiple modalities are combined to provide complimentary and/or overlapping data sets. For example, MR scanning generally provides soft tissue morphological data and provides greater resolution of structural and functional characteristics of soft tissue, etc. PET scanning generally has a lower resolution but provides more useful information regarding the functional condition of the body tissues and systems such as the cardiovascular system. PET scanning is superior for indicating the presence of tumors or decreased blood flow to certain organs or areas of the body. The complementary strengths of two or more imaging modalities can be provided simultaneously by performing both methods in a single apparatus and imaging session.

During operation, image quality of one or more imaging modalities, such as a PET modality, can be affected by motion during imaging, for example, respiratory motion. When using a PET modality, imaging artifacts may be generated during image acquisition because of the respiratory motion. In multi-modality systems, the PET modality requires a relatively long duration data acquisition period, on the order of several minutes (e.g., about 2 to 30 minutes per image) for a typical clinically sufficient image. Typically, a large number of PET data acquisitions (e.g., frames) are acquired at many different time points during this period. Consequently, patient movement is a problem in PET scanning.

PET scanning has a limited field of view (FOV) and cannot capture whole body images. In order to perform whole body imaging, multiple PET images are captured at multiple positions with respect to a patient (e.g, beds). When stitching together multiple beds to form a single whole body PET image, motion effects and attenuation are most pronounced at the edges of the FOV (e.g., the edge voxels/slices). In multi-bed studies, breathing patterns of the patient can change between beds. Therefore, detection and compensation for the varying respiratory patterns is important for whole body PET reconstruction.

Single bed elastic motion correction algorithms are increasingly being used to model and compensate for respiratory motion in clinical PET images. If motion effects are not properly accounted for, image non-uniformity and incorrect quantification will occur. Although single bed elastic motion correction has been applied, motion correction for multi-bed PET data has remained challenging.

SUMMARY

In some embodiments of the present disclosure, a method of processing data for medical imaging is disclosed. The method comprises providing a first set of first modality data including a first mu-map, a first plurality of gated data, and a first plurality of motion vectors. The first set of first modality data is generated by a first imaging modality of an imaging system. A first plurality of attenuation maps is generated from the first set of first modality data. Each of the first plurality of attenuation maps corresponds to a gate in the first plurality of gated data. A first set of second modality data is provided including a first plurality of frames. Each of the first plurality of frames corresponds to one of the first plurality of attenuation correction maps. The first set of second modality data is generated by a second imaging modality of an imaging system. The first plurality of frames are warped by corresponding motion vectors from the first plurality of motion vectors. The first plurality of warped frames are combined into a first single-bed image.

In some embodiments of the present disclosure, a non-transitory, computer readable medium storing computer executable instructions is disclosed. The computer executable instructions cause a computer to receive a first set of first modality data including a first mu-map and a first plurality of gated data, and a first plurality of motion vectors. The first set of first modality data is generated by a first imaging modality of an imaging system. The computer generates a first plurality of attenuation maps from the first set of first modality data. Each of the first plurality of attenuation maps corresponds to a gate in the first plurality of gated data. A first set of second modality data is received including a first plurality of frames. Each of the first plurality of frames corresponds to one of the first plurality of attenuation correction maps. The first set of second modality data is generated by a second imaging modality of an imaging system. The computer warps the first plurality of attenuation maps by corresponding motion vectors from the first plurality of motion vectors and combines the first plurality of warped frames into a first single-bed image.

In some embodiments of the present disclosure, a system for medical imaging is disclosed. The system comprises a first imaging modality, a second imaging modality, and a computer in data communication with the first imaging modality and the second imaging modality. The computer is configured to process data for medical imaging by receiving a first set of first modality data including a first mu-map, a first plurality of gated data from the first imaging modality, and a first plurality of motion vectors. The computer generates a first plurality of attenuation maps from the first set of first modality data. Each of the first plurality of attenuation maps corresponds to a gate in the first plurality of gated data. A first set of second modality data is received from the second imaging modality. The first set of second modality data includes a first plurality of frames. Each of the first plurality of frames corresponds to one of the first plurality of attenuation correction maps. The computer warps the first plurality of attenuation correction maps by corresponding motion vectors from the first plurality of motion vectors and combines the first plurality of warped frames into a first single-bed image.

BRIEF DESCRIPTION OF THE DRAWINGS

The following will be apparent from elements of the figures, which are provided for illustrative purposes and are not necessarily to scale.

FIG. 2A illustrates one embodiment of a single-bed PET-based mu-map.

FIG. 2B illustrates one embodiment of an elongated MR based mu-map.

FIG. 2C illustrates one embodiment of an elongated MR-based motion vector map overlayed on a mu-map having the same dimensions as the PET-based mu-map of FIG. 2A.

DETAILED DESCRIPTION

This description of the exemplary embodiments is intended to be read in connection with the accompanying drawings, which are to be considered part of the entire written description.

Various embodiments of the present disclosure address the foregoing challenges associated with motion correction for whole body combined imaging, for example, by utilizing a new motion correction algorithm that incorporates the motion vectors from multiple beds during whole body assembly.

Figure 1:
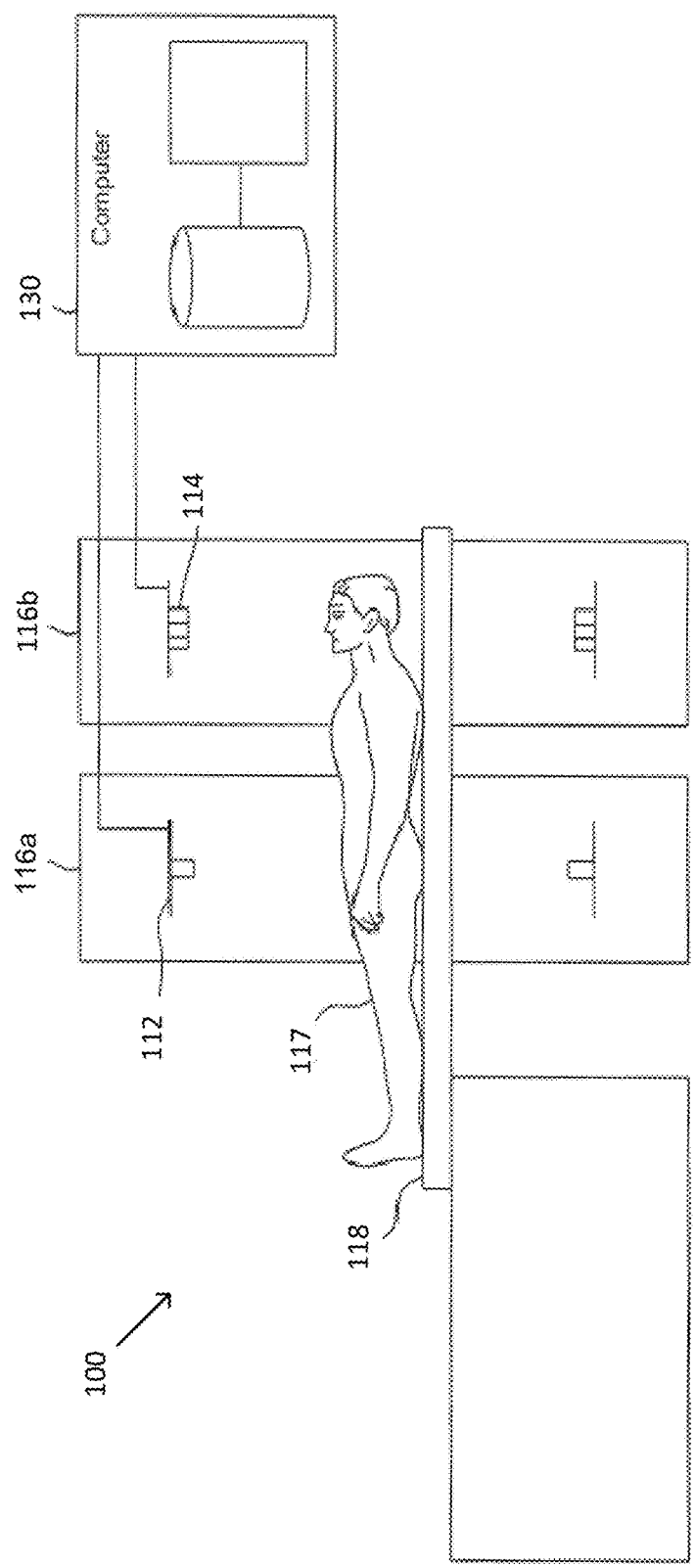
FIG. 1 illustrates one embodiment of a multi-modality imaging apparatus.

FIG. 1 shows one example of a multi-modality imaging apparatus 100 (such as, for example, a combination MR/PET apparatus). The multi-modality imaging apparatus 100 may be configured for two or more imaging modalities, such as, for example, combined PET/MR, PET/CT, SPECT/MR, SPECT/CT, and/or any other suitable combined diagnostic imaging modalities. The multi-modality imaging apparatus 100 includes a scanner for at least a first imaging modality 112 provided in a gantry 116a and a scanner for a second imaging modality 114 provided in a second gantry 116b. In various embodiments, PET and MR are described as examples of first and second imaging modalities that may be used in various embodiments, but they are non-limiting examples. A patient 117 lies on a movable patient bed 118 that may be movable between the gantries. Alternatively, the two imaging modalities 112 and 114 may be combined together in a single gantry.

Scan data from at least the first and second imaging modalities 112, 114 are stored at one or more computer databases 140 and processed by one or more computer processors 150 of a computer 130. Scan data from the first and second imaging modalities may be stored in the same database 140 or in separate databases. The graphical depiction of computer 130 in FIG. 1 is provided by way of illustration only, and computer 130 may include one or more separate computing devices. In some embodiments, the computer 130 is configured to generate a whole body reconstructed image from a first modality data set and a second modality data set. The first and second modality data sets can be provided by the first imaging modality 112 and the second imaging modality 114 and/or may be provided as a separate data set, such as, for example, from memory coupled to the computer 130.

In some embodiments, the first and second imaging modalities 112, 114 are MR and PET, respectively. For example, a patient can be scanned with the first imaging modality 112 and the second imaging modality 114 to yield MR 3D morphological data and PET acquisition and physiological waveform data, respectively. The scans may be performed sequentially, with a PET scan following a MR scan, and/or simultaneously. In another embodiment, the first imaging modality is PET and the second imaging modality is MR.

In some embodiments, gating is performed based on an acquired physiological signals to determine gate locations (in time) and a width (in time duration) for the gates. Any gating algorithm known in the art can be used for this purpose. Gate width (the time duration of a gate) depends on the imaging modality. The widths (time durations) of respective gates in a cycle may be constant or may vary, e.g., depending on the gating algorithm that is used and the constraints of the imaging modality.

Although combined MR and PET data is discussed herein, it will be recognize that the disclosed systems and methods are applicable to any combined modalities, such as, for example, MR/PET, CT/PET, MR/SPECT, and/or CT/SPECT.

In some embodiments, the first and second imaging modalities 112, 114 each comprise a FOV. The FOV determines a width of an image obtainable by the first or second imaging modality 112, 114. In some embodiments, the FOV of the first imaging modality 112 is greater (e.g., longer) than the FOV for the second imaging modality 114. For example, in some embodiments, the first FOV has a greater length with respect to attenuation and/or motion vectors. In some embodiments, the first imaging modality 112 is an MR scan with a FOV of about 45 cm and the second imaging modality 114 is a PET scan with a FOV of less than 45 cm, such as, for example, less than about 25 cm, less than about 16 cm, and/or any FOV less than the FOV of the first imaging modality 112. In some embodiments, the FOV of the imaging modality is less than total area to be imaged. For example, in some embodiments, the second imaging modality is a PET imaging modality having a FOV of about 25 cm. In order to generate a whole body image, multiple beds (e.g., imaging positions) are acquired for at least the second imaging modality 114 and stitched together to generate the whole body image.

In some embodiments, the greater FOV of the first imaging modality 112 is used to compensate for attenuation and/or motion at the edge slices of the second imaging modality 114. The first imaging modality 112 includes a larger FOV than the second imaging modality 114 and is configured to capture one or more elongated (or expanded) parameters, such as, for example, an elongated mu-map, elongated motion vectors, an expanded sensitivity term, and/or any other suitable elongated or expanded parameters. In some embodiments, the elongated parameters are derived from the first imaging modality data and/or the second imaging modality data. The elongated parameters generated by the first imaging modality 112 are used for motion correction of the second imaging modality 114.

For example, FIG. 2A illustrates one embodiment of a PET mu-map 200 having a FOV of 25 cm. The edges of the PET mu-map 200 would overlap with the edges of subsequent PET mu-maps captured for subsequent beds. Breathing patterns of a patient can change between beds, resulting in artifacts during a whole body reconstruction process due to mismatched motion vectors in the PET mu-map 200a and 3D sensitivity terms of the PET imaging modality. By utilizing a mu-map, motion vectors, 3D sensitivity term, and/or a reconstruction volume with a longer FOV during reconstruction, the artifacts generated during whole body reconstruction are reduced.

FIG. 2B illustrates one embodiment of an elongated MR-based motion vector map 200b overlaid on a mu-map having the same dimensions as the PET-based mu-map 200 of FIG. 2A. In. The greater FOV 202b of the MR-derived motion vector map 200c allows the motion vectors for the edges of the PET data 200a to be easily determined. The motion vector information of the larger MR-derived mu-map 200b is used to compensate for motion and attenuation in the PET data 200a during whole body image reconstruction.

FIG. 2C illustrates a longer MR-based mu map 200c. The MR-based mu-map 200c has a FOV 202b greater than the FOV of the PET-based mu-map 200a, such as, for example, 33 cm. Motion vectors for the edge slices of the PET-based mu-map 200a can be derived from the MR-based gated images 200c. In some embodiments, the longer mu-map and motion vectors from an MR imaging modality is used to reconstruct a motion corrected single bed PET image.

Figure 3:
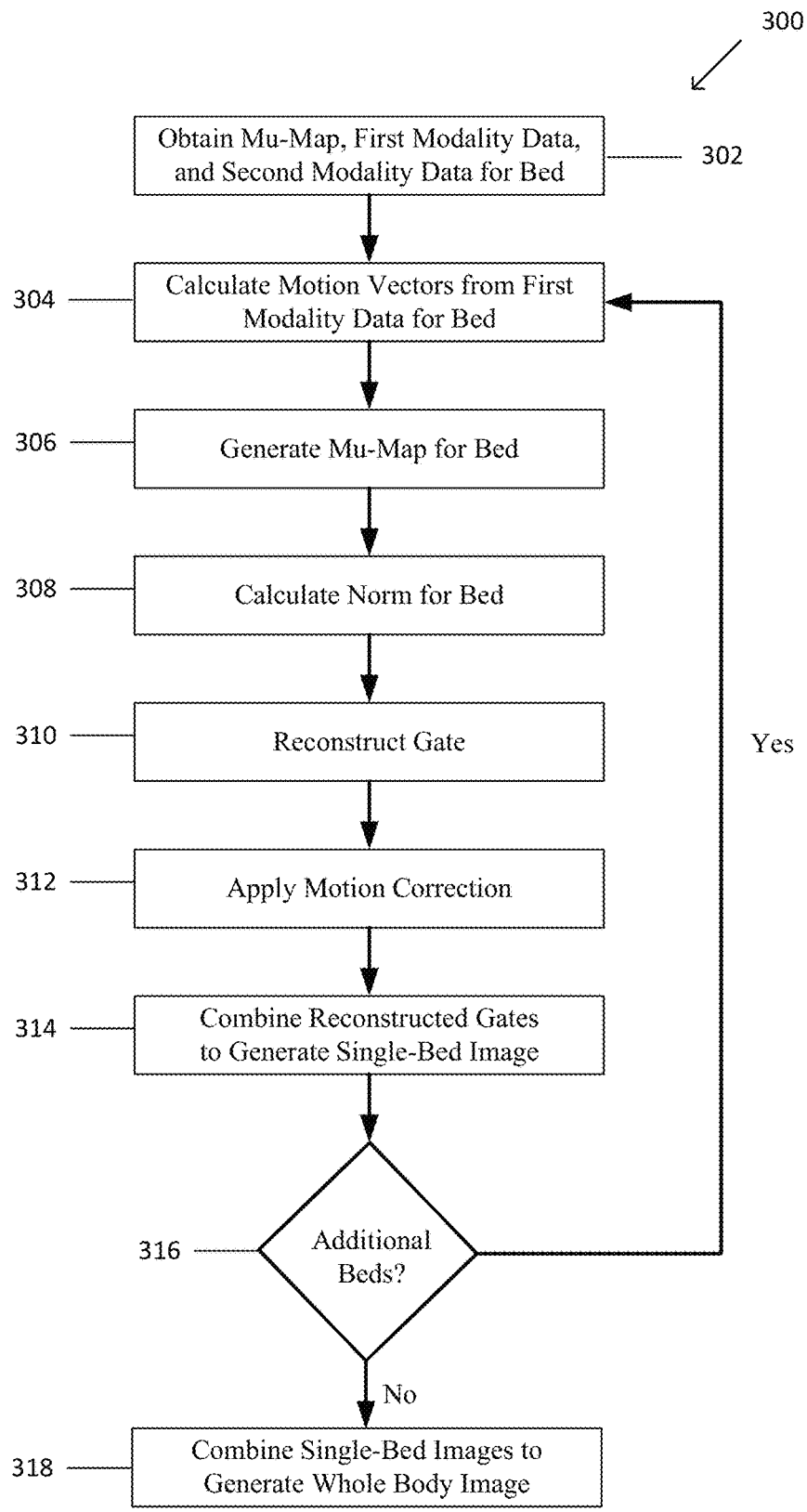
FIG. 3 illustrates one embodiment of a method for multi-bed motion corrected reconstruction.

FIG. 3 illustrates one embodiment of a method 300 for generating a whole body, multi-bed, elastic motion corrected image from a multi-bed scan. In a first step 302, dual-modality data, such as, for example, gated MR data and PET data, is provided to the computer 130. In some embodiments, the dual-modality data is acquired by a first imaging modality 112 and a second imaging modality 114 of a multi-modality imaging apparatus 100. The dual modality data may be acquired sequentially and/or simultaneously. In some embodiments, the dual-modality data includes pre-captured data provided to the computer 130, by, for example, a memory unit coupled to the computer 130. The dual-modality data includes two or more beds. For example, in one embodiment, a self-gated radial VIBE MRI sequence is used to generate gated MR images for a first bed and a second bed. PET data is acquired as list-mode PET data for both the first bed and the second bed simultaneously with the acquisition of the MR data. In some embodiments, the first modality data includes an elongated mu-map generated prior to, simultaneously with, and/or following acquisition of the dual-modality data.

In a second step 304, motion vectors are calculated from the first modality data for each frame of a first bed. In some embodiments, the first modality data is binned (e.g., gated) and reconstructed into discrete states of a motion cycle, such as, for example, a respiratory cycle, for each bed. Motion vectors are calculated for each frame of the gated data. The motion vectors may be calculated using image registration based on one or more algorithms, such as diffeomorphic demons algorithm. In some embodiments, the first modality data comprises gated MR images. The motion vectors of the MR images are derived by means of post-processing and registration of the high resolution MR images to the reference gate of each bed. In some embodiments, motion vectors may be calculated from the first modality data, the second modality data, and/or jointly estimated using both the first modality data and the second modality data.

In some embodiments, the second modality data, for example, list-mode PET data, is divided into predetermined frames based on the amplitude of the motion waveform for the current bed (e.g., the discrete bins generated for the first modality data). In a third step 306, an attenuation correction map (mu-map) is generated for each frame of the bed from the first modality data. The attenuation correction map is generated by warping the first modality mu-map, for example, an elongated MR-based mu-map, with the derived motion vectors for the specific frame. FIG. 2C illustrates one embodiment of an elongated MR-based mu-map 200c. The longer FOV 202b of the MR-based mu-map 200c enables accurate modeling of the motion vectors from adjacent beds, which are used as weighting terms when stitching multiple images of the second image modality together (e.g., combining a first PET bed image with a second PET bed image). The elongated motion vectors and/or attenuation correction maps (e.g., bed-by-bed mu-maps) of the first imaging modality 112 eliminate attenuation mismatch at the edge of each bed of the second imaging modality 114 caused by motion, such as, respiratory motion. In some embodiments, the length of the frames for the various datasets from the first and second imaging modalities 112, 114 can be longer than required for a single bed position. The elongated length enables using additional information from one or more slices/voxels outside the single bed FOV so as to reduce artifacts in the edge slices/voxels. If the additional slices are not available from one modality, for example the second imaging modality 114, estimates of the missing region may be calculated using data from the other imaging modality, for example, the first imaging modality 112. In some embodiments, a truncated part estimate may be calculated using an image, mu-maps and/or motion vectors.

Referring back to FIG. 3, in a fourth step 308, a norm for each gate is determined. In a fifth step 310, each gate (e.g., each discrete state of the respiratory cycle) is reconstructed from the elongated motion vectors and/or mu-maps, the derived gate norm, and a plurality of second-modality data for each gate. The plurality of second-modality data may comprise, for example, one or more sinograms. A sinogram comprises annihilation event data acquired over a sub-period of a gate. For example, each gate may comprise one or more sinograms captured during consecutive time periods. In some embodiments, the second modality data comprises PET sinogram data. In a sixth step 312, motion correction is applied to each reconstructed gate to compensate for movement of the patient. Motion correction may be applied by utilizing an inverse motion vector to compensate for motion, such as respiratory motion, during the gate period (see Equation 2 below). In some embodiments, depending on the amplitude of the motion vectors and/or the size of the reconstructed FOV along the z-axis, some of the voxels at the edge of the planes could lie outside the single-bed FOV of the second imaging modality. To improve the signal to noise ratio (SNR) of the final motion corrected reconstructed image, the individual frames of each bed are warped to a reference frame and are summed together. The 3D spatial motion warping operation from frame n to frame m can be denoted as:

$$f_{m,b}^{mc} = T_{m,n,b}(\bar{x}) \cdot f_{n,b}(\bar{x}) \qquad \text{(Equation 1)}$$

where $f(\bar{x})$ is a discretized version of the time varying 3D image for frame m and bed b while $\bar{x}$ is the center of the $j^{th}$ voxel (j=1 . . . J), T(x) is a warping function from frame n to frame m, and M is the total number of frames summed for a specific bed. In some embodiments, one or more of the terms in the 3D spatial motion warping operation, the attenuation data, and/or the measured data may be larger than a scanner FOV of one or more of the imaging modalities 112, 114 and/or a desired reconstructed FOV. By using a larger FOV than the scanner FOV and/or the desired reconstructed FOV, the 3D spatial warping operation ensures that no truncation artifacts are generated at the edges of the reconstructed gated images. In some embodiments, an expanded PET FOV and an expanded sensitivity term are generated from adjacent bed motion vectors and sensitivity terms. The expanded PET FOV and sensitivity terms accounts for variation in a motion pattern, such as, for example, a respiratory pattern, as well as variation in the sensitivity term between beds.

In a seventh step 314, after the each of the reconstructed gate images are motion corrected, each reconstructed frame is combined, or summed, to generate a single-bed image. In some embodiments, the individual frames are warped (e.g., motion corrected) and summed together in a single step using post-reconstruction motion correction according to the equation:

$$\frac{\sum_{n=1}^{M}(T_{m,n,b}(\bar{x})(f_{n,b}(\bar{x}) \cdot r_{n,b}(\bar{x}) \cdot d_{n,b}(\bar{x})))}{\sum_{n=1}^{M}((T_{m,n,b}(\bar{x})(r_{n,b}(\bar{x}) \cdot d_{n,b}(\bar{x}))))}$$ (Equation 2)

where $r(\bar{x})$ is a sensitivity weighting term and $d(\bar{x})$ is the frame duration. In some embodiments, the sensitivity term may be larger than a scanner FOV. Modeling of motion vectors using an enlarged sensitivity term can provide a more accurate reconstruction.

In an eight step 316, the computer 130 checks if any beds remain to be processed. The second through seventh steps 304-314 of the method 300 are repeated for each bed in the dual-modality data. For example, in one embodiment, a first bed and a second bed are obtained by the multi-modality imaging apparatus 100. The computer 130 processes data corresponding to the first bed to generate a single-bed image for the first bed according to steps two through seven 304-314 discussed above. The computer 130 processes the second bed to generate a single-bed image for the second bed according to steps two through seven 304-314. Although the method is discussed herein as processing each bed sequentially, it will be recognized that the computer 130 can process two or more of beds in serial and/or parallel.

Figure 4A:
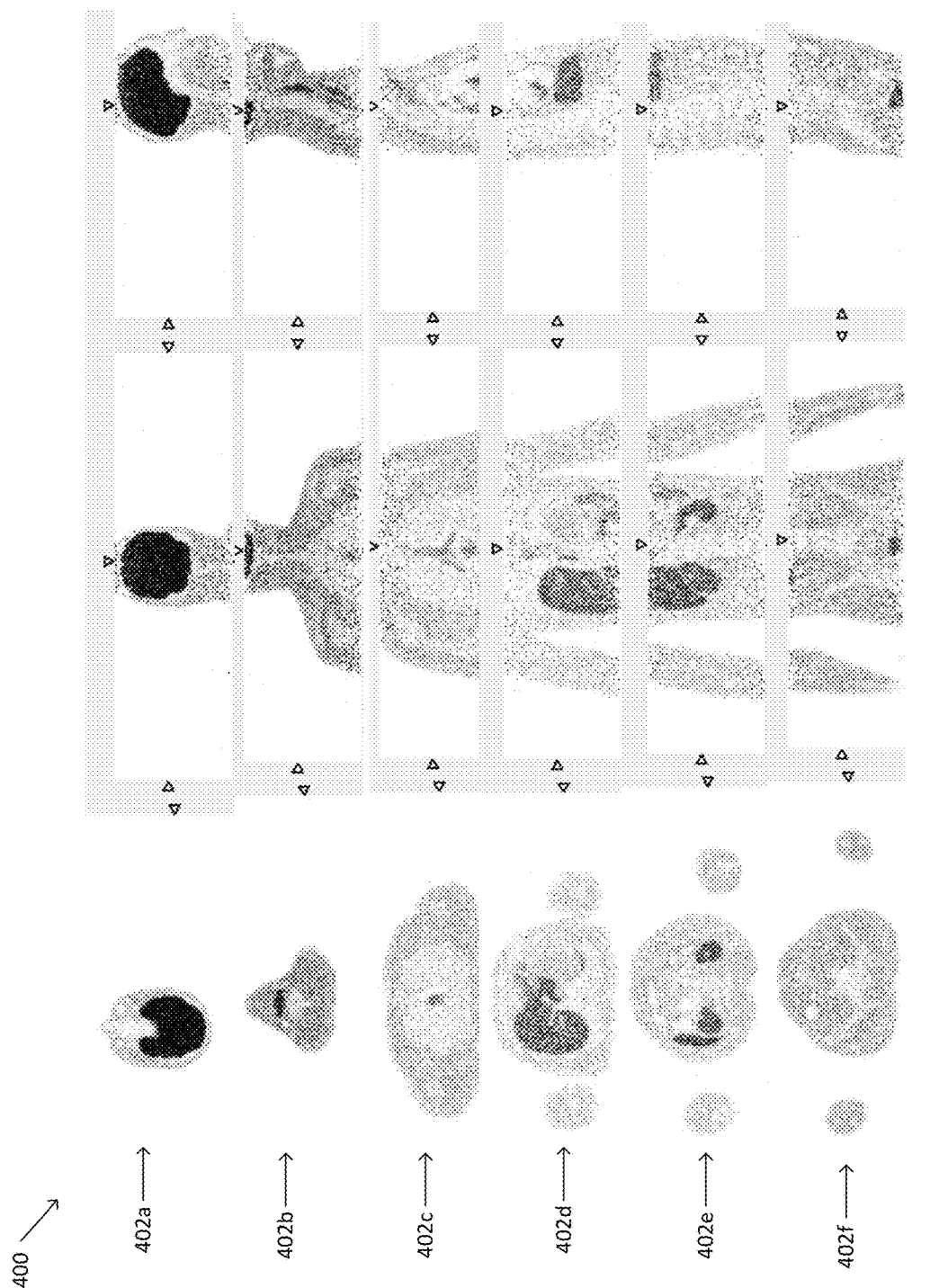
FIG. 4A illustrates one embodiment of a bed-by-bed reconstructed image.

FIG. 4A illustrates one embodiment of a bed-by-bed reconstructed image 400 including six-beds 402a-402f. In the illustrated embodiment, the bed-by-bed reconstructed image is generated using an elongated mu-map and motion vectors in conjunction with a modification to a 3D sensitivity term to generate motion corrected PET images. Each bed 402a-402f is generated by summing together a plurality of frames according to the method described above. As shown in FIG. 4A, in some embodiments, each bed includes an overlapping portion with the previous and subsequent frames (if present). FIG. 4A illustrates a max diaphragm respiratory motion of 2.5 cm and an anterior-posterior chest expansion of 1.2 cm having a respiratory cycle of 5 cm. Although specific parameters are shown herein, it will be recognized that the disclosed methods are suitable for any amount of diaphragm and/or anterior-posterior motion over a respiratory cycle of any duration.

After all beds in the dual-modality data set have been processed, each of the single-bed images are stitched, or summed, together to generate a multi-bed motion corrected full-body reconstruction in a ninth step 318. The motion corrected image from each bed is stitched together by modeling the effects of motion in the 3D sensitivity map of each bed and frame. For example, in some embodiments, the full body motion corrected image is generated according to the equation:

$$f^{pmc}(\bar{x}) = \frac{\sum_{b=1}^{B}\sum_{n=1}^{M}(T_{m,n,b}(\bar{x})(f_{n,b}(\bar{x}) \cdot r_{n,b}(\bar{x}) \cdot d_{n,b}(\bar{x})))}{\sum_{b=1}^{B}\sum_{n=1}^{M}((T_{m,n,b}(\bar{x})(r_{n,b}(\bar{x}) \cdot d_{n,b}(\bar{x}))))}$$ (Equation 3)

Figure 4B:
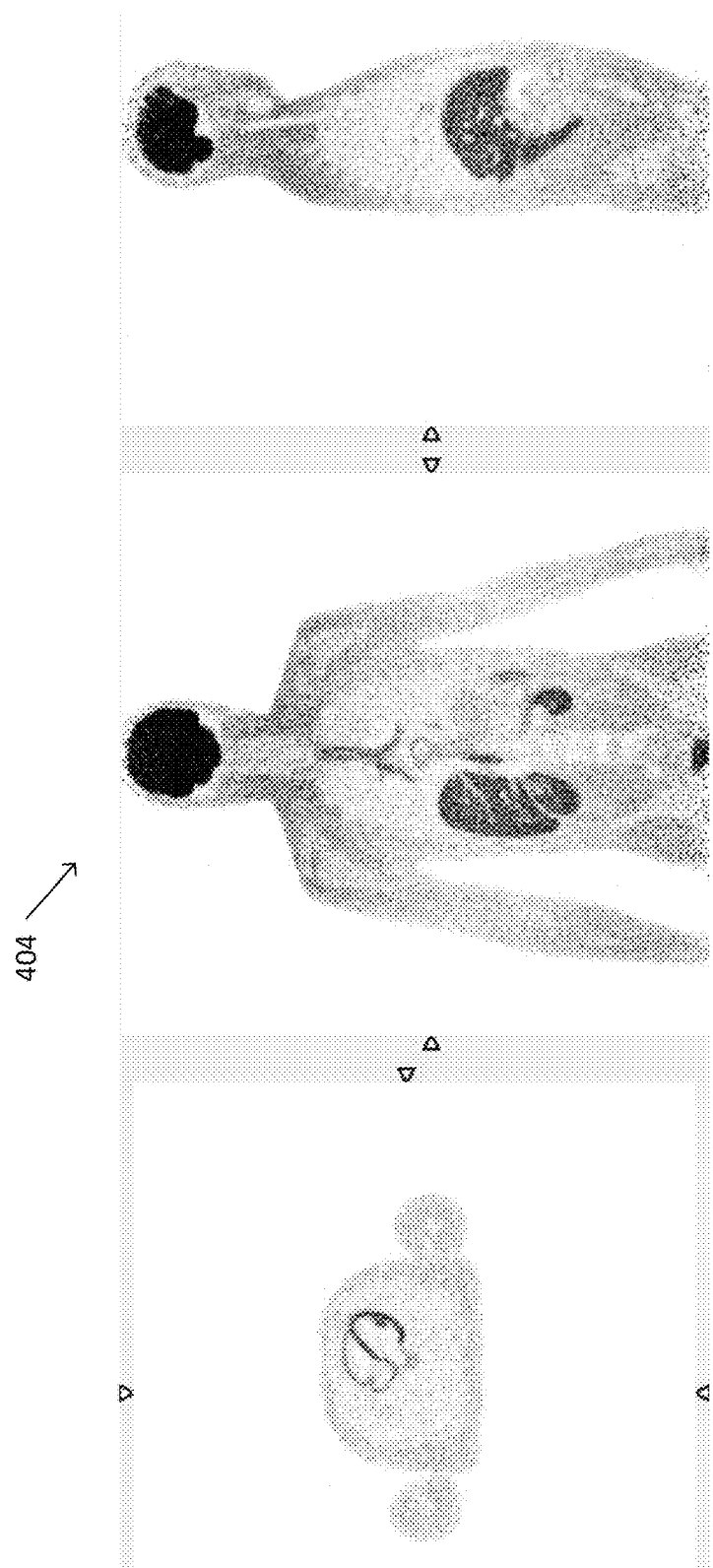
FIG. 4B illustrates one embodiment of a motion corrected whole body reconstructed image according to the methods described herein.

The number of motion corrected frames m=1 ... $M_b$ and/or the scan duration of each frame d=1 ... $D_{m,b}$ in each bed can be independent of each other. Although the seventh step 314, the eight step 316, and the ninth step 318 of the method 300 are discussed herein as discrete steps, it will be recognized that the steps 314-318 may be combined into a single step, for example, utilizing the equation above. FIG. 4B illustrates one embodiment of a whole body stitched image 404 generated from the six beds 402a-402f illustrated in FIG. 4A. The use of elongated mu-maps and motion vectors of the first image modality (e.g., MR-based mu-maps) eliminates attenuation mismatch at the edge of each bed of the second imaging modality (e.g., PET data), for example caused by respiratory motion, which reduces the generation of artifacts in a whole body image.

Figure 5A:
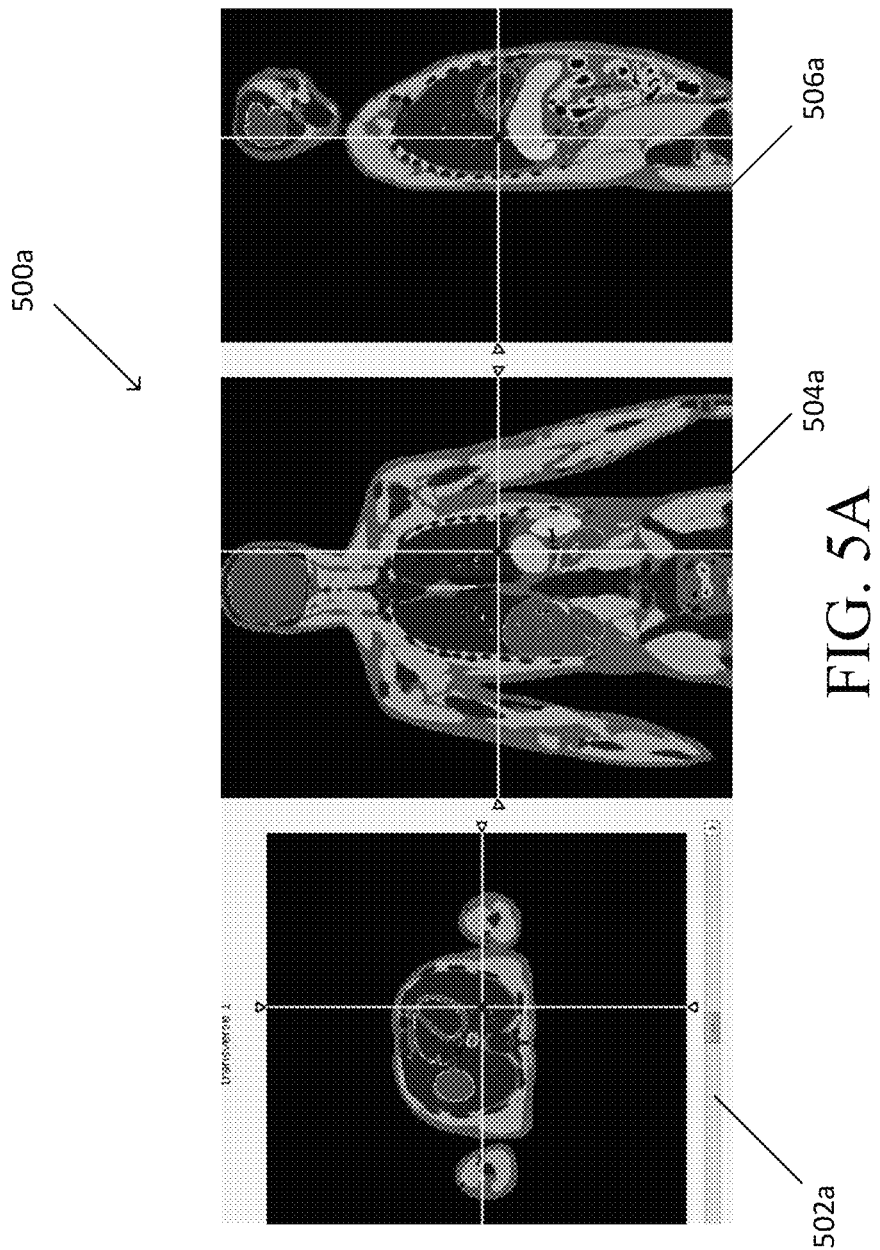
FIG. 5A illustrates one embodiment of a non-uniform rational B-spline (NURBS)-based cardiac-torso (NCAT) phantom.
Figure 5B:
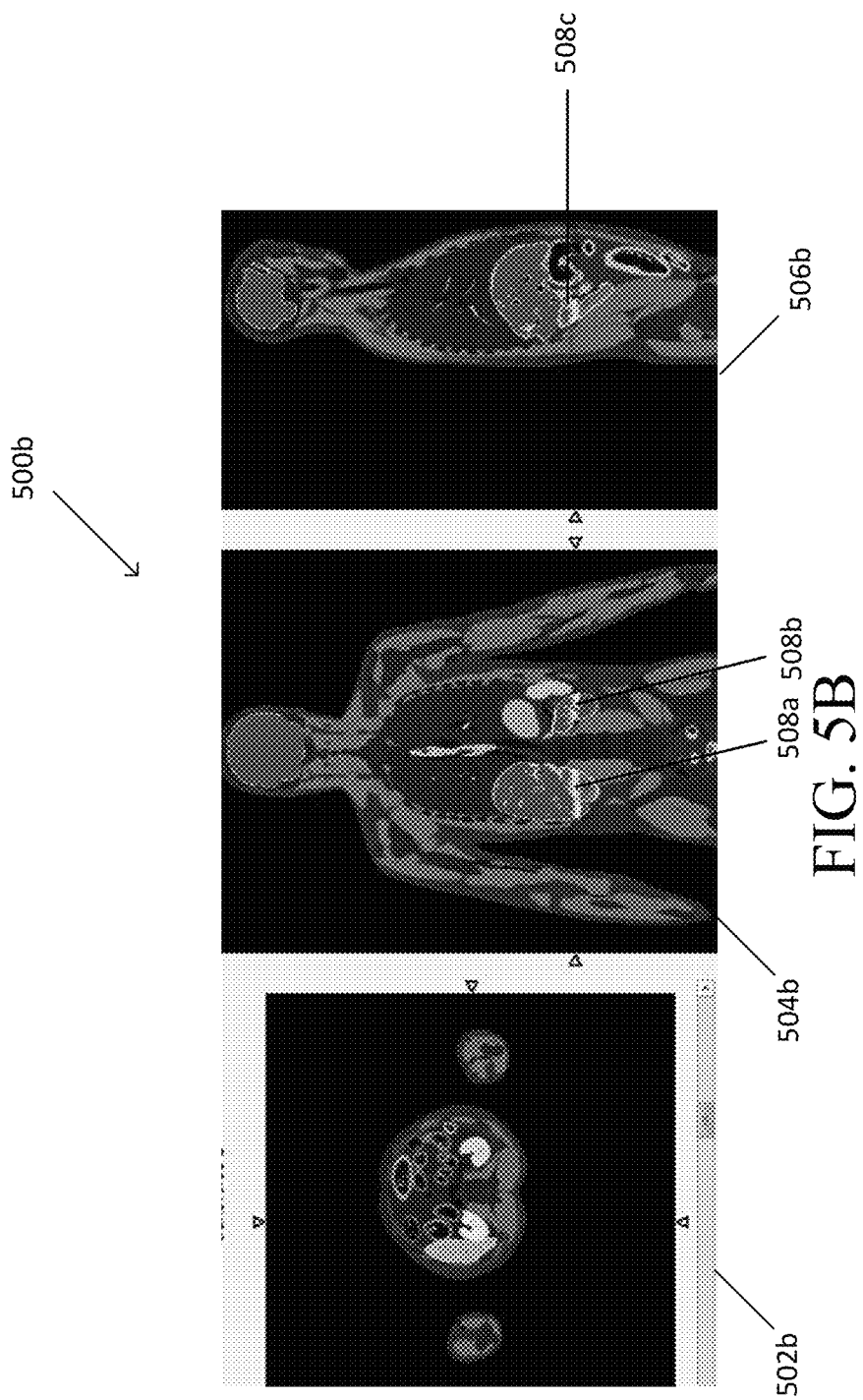
FIG. 5B illustrates one embodiment of a whole body image generated using a single bed based motion field.

FIG. 5A illustrates one embodiment of a non-uniform rational B-spline (NURBS)-based cardiac-torso (NCAT) phantom shown in ideal whole body image 500a. The NCAT phantom is used in evaluation to illustrate a best-case (or ground truth) and is used to detect any errors in a reconstructed image. FIG. 5B illustrates one embodiment of a whole body reconstructed image 500b generated using a single bed based motion field. The use of a single bed based motion field in reconstruction can generate artifacts in the image. The whole body reconstructed image 500b was reconstructed without the use of an adjusted sensitivity term based on adjacent motion vectors and without elongated mu-maps. As can be seen in FIG. 5B, the whole body reconstructed image 500b contains multiple artifacts 502a, 502b, 502c generated during the reconstruction process. The artifacts 502a-502c are generated due to motion change between beds and attenuation of the edge voxels of the second imaging modality 114.

Figure 5C:
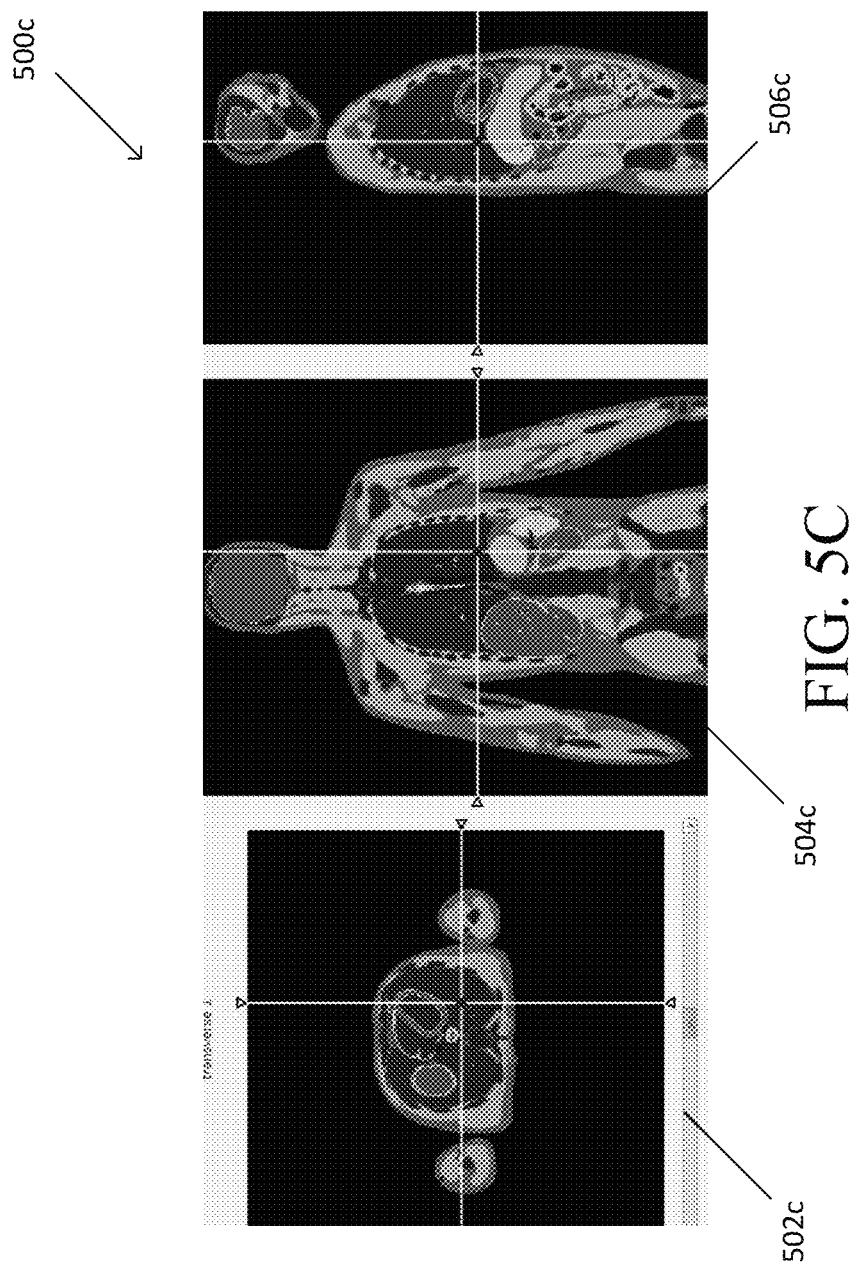
FIG. 5C illustrates one embodiment of a whole body reconstructed image generated according to the methods described herein.

FIG. 5C illustrates one embodiment of a whole body reconstructed image 500c generated according to the present method. The whole body reconstructed image 500c eliminates the artifacts shown FIG. 5B and provides a whole body reconstructed image 500c that is substantially identical to the ideal NCAT phantom 500a of FIG. 5A. As shown in FIG. 5C, the methods disclosed herein produce a whole body reconstructed image 500c substantially free of defects. The use of an elongated mu-map, motion vectors, and sensitivity terms allows the disclosed method to compensate for motion mismatch between multiple beds in the second modality data.

Figure 6:
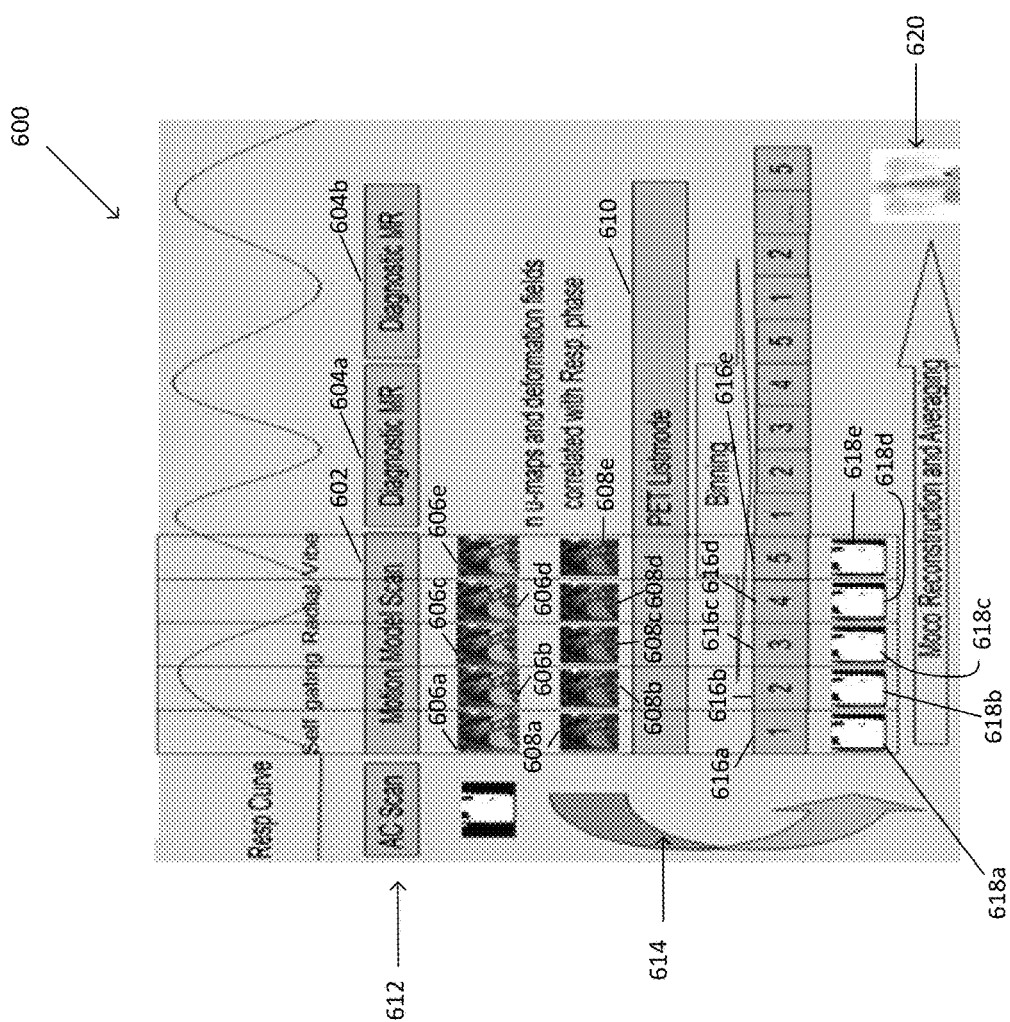
FIG. 6 illustrates one embodiment of a schematic representation of an MR-PET workflow for generating a motion corrected whole body image.

FIG. 6 illustrates one embodiment of a schematic representation of an MR-PET workflow 600 for generating a multi-bed elastic motion corrected whole body image, such as, for example, the whole body reconstructed image 500c illustrated in FIG. 5C. As shown in FIG. 6, a mu-model scan 602 is performed by an MR imaging modality 612. The MR imaging modality 612 acquires one or more mu-maps 606a-606e with a FOV having a first length. The generated mu-maps 606a-606e are processed to generate motion vector maps 608a-608e and are correlated with respiratory motion phases. In some embodiments, a longer single mu-map is acquired and one or more motion vectors are used to generate a series of mu-maps that correspond to each frame. After performing the mu-model scan 602, the MR imaging modality 612 captures diagnostic MR data 604a, 604b. Simultaneously with the acquisition of mu-model data 602 and diagnostic MR data 604a, 604b, a PET imaging modality 614 captures PET list-mode data 610. The PET list-mode data 610 is divided into a plurality of bins 616a-616e corresponding to the respiratory phases identified by the mu-maps 606a-606e. A plurality of single-frame PET images 618a-618e are generated by combining the PET list-mode data 614 with the MR-based mu-maps 606a-606e. The single-frame PET images 618a-618e are combined according to the method 300 illustrated in FIG. 3 to generate single-bed PET images and/or a whole body elastic motion corrected image 620.

Figure 7:
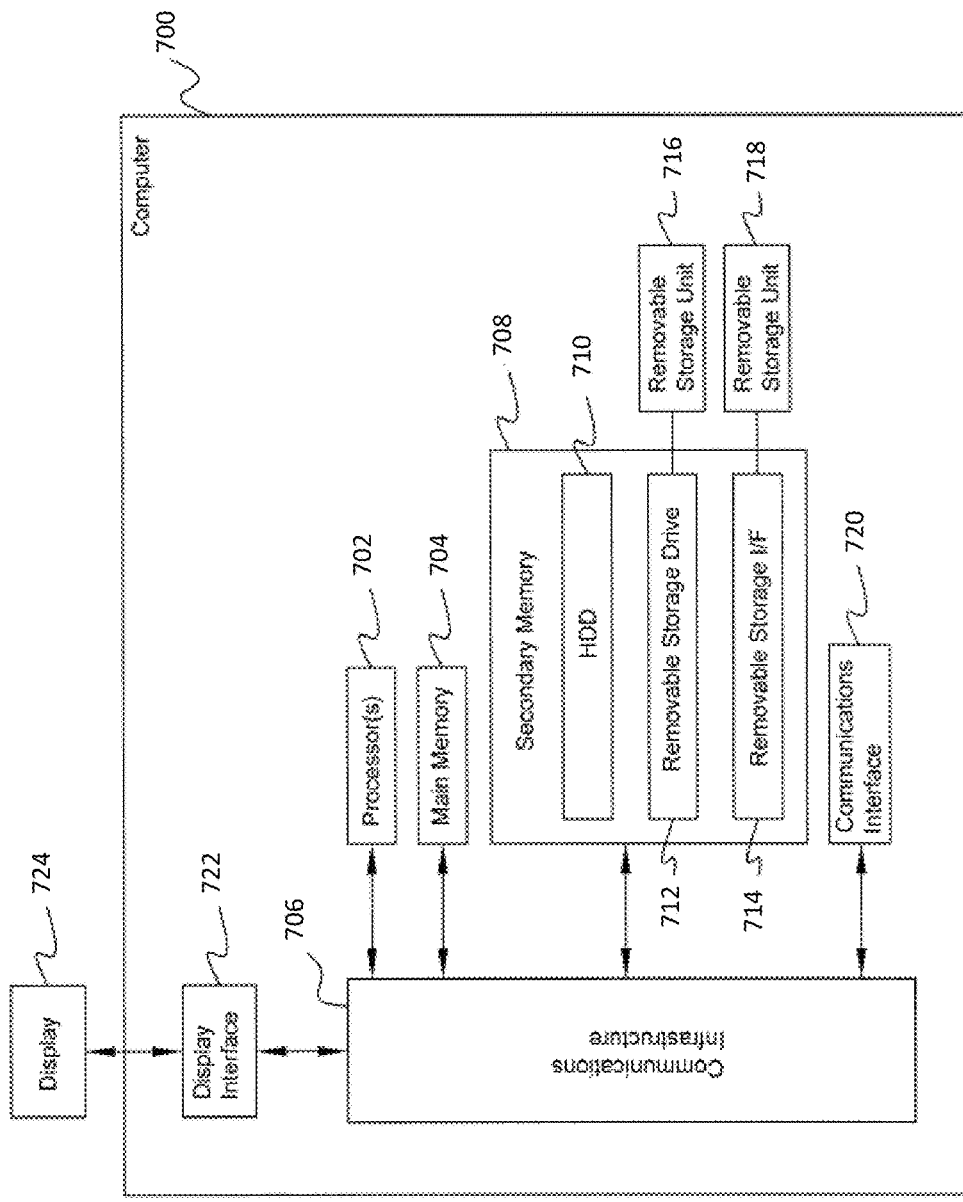
FIG. 7 is a block diagram of one embodiment of a computer system configured to execute one or more steps of the methods described herein.

FIG. 7 is an architecture diagram of a computer system 700 that may be used in some embodiments, e.g., for implementing computer 130 shown in FIG. 1. Computer system 700 may include one or more processors 702. Each processor 702 is connected to a communication infrastructure 706 (e.g., a communications bus, cross-over bar, or network). Computer system 700 may include a display interface 722 that forwards graphics, text, and other data from the communication infrastructure 706 (or from a frame buffer, not shown) for display on the display unit 724 to a user.

Computer system 700 may also include a main memory 704, such as a random access memory (RAM), and a secondary memory 708. The main memory 704 and/or the secondary memory 708 comprise non-transitory memory. The secondary memory 708 may include, for example, a hard disk drive (HDD) 710 and/or removable storage drive 712, which may represent a floppy disk drive, a magnetic tape drive, an optical disk drive, a memory stick, or the like as is known in the art. The removable storage drive 712 reads from and/or writes to a removable storage unit 716. Removable storage unit 716 may be a floppy disk, magnetic tape, optical disk, or the like. As will be understood, the removable storage unit 716 may include a computer readable storage medium having tangibly stored therein (embodied thereon) data and/or computer software instructions, e.g., for causing the processor(s) to perform various operations.

In alternative embodiments, secondary memory 708 may include other similar devices for allowing computer programs or other instructions to be loaded into computer system 700. Secondary memory 708 may include a removable storage unit 718 and a corresponding removable storage interface 714, which may be similar to removable storage drive 712, with its own removable storage unit 716. Examples of such removable storage units include, but are not limited to, USB or flash drives, which allow software and data to be transferred from the removable storage unit 716, 718 to computer system 700.

Computer system 700 may also include a communications interface (e.g., networking interface) 720. Communications interface 720 allows software and data to be transferred between computer system 700 and external devices. Examples of communications interface 720 may include a modem, Ethernet card, wireless network card, a Personal Computer Memory Card International Association (PCMCIA) slot and card, or the like. Software and data transferred via communications interface 720 may be in the form of signals, which may be electronic, electromagnetic, optical, or the like that are capable of being received by communications interface 720. These signals may be provided to communications interface 720 via a communications path (e.g., channel), which may be implemented using wire, cable, fiber optics, a telephone line, a cellular link, a radio frequency (RF) link and other communication channels.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of processing data for medical imaging, the method comprising:
providing a first set of first modality data including a first mu-map, a first plurality of gated data, and a first plurality of motion vectors, wherein the first set of first modality data is generated by a first imaging modality of an imaging system;
providing a first set of second modality data including a first plurality of frames, wherein each of the first plurality of frames corresponds to one of the first plurality of attenuation correction maps, and wherein the first set of second modality data is generated by a second imaging modality of an imaging system;
warping the first plurality of frames by one or more motion vectors from the first plurality of motion vectors;
combining the first plurality of warped frames into a first single-bed image
providing a second set of first modality data including a second mu-map, a second plurality of motion vectors and a second plurality of gated data;
providing a second set of second modality data including a second plurality of frames, wherein each of the second plurality of frames corresponds to one or more of the second plurality of motion vectors;
warping the second plurality of frames by one or more motion vectors from the plurality of motion vectors;
combining the second plurality of warped frames into a single-bed image; and
combining the first single-bed image and the second single-bed image into a whole body image.

2. The method of claim 1, wherein the first plurality of image frames comprise sinograms.

3. The method of claim 1, wherein generating the first single-bed image and the second-single bed image comprises applying an expanded sensitivity term and summing the respective plurality of warped frames.

4. The method of claim 1, comprising:
generating a first plurality of attenuation maps from the first set of modality data, wherein each of the first plurality of attenuation maps corresponds to a gate in the first plurality of gated data; and warping the first plurality of frames by a corresponding attenuation map from the first plurality of attenuation maps.

5. The method of claim 4, wherein the first plurality of attenuation correction maps are generated by warping an ungated attenuation map by a plurality of elongated motion vectors corresponding to respiratory motion derived from the first set of first modality data.

6. The method of claim 1, wherein the whole body image is generated according to the equation:

$$f^{prmc}(\overline{x}) = \frac{\sum_{b=1}^{B}\sum_{n=1}^{M}(T_{m,n,b}(\overline{x})(f_{n,b}(\overline{x}) \cdot r_{n,b}(\overline{x}) \cdot d_{n,b}(\overline{x})))}{\sum_{b=1}^{B}\sum_{n=1}^{M}((T_{m,n,b}(\overline{x})(r_{n,b}(\overline{x}) \cdot d_{n,b}(\overline{x}))))}$$

where $r(\overline{x})$ is the sensitivity weighting term, $d(\overline{x})$ is a frame duration, m is the number of image frame, $f(\overline{x})$ is a discretized version of frame m and bed b, $\overline{x}$ is a center of a $j^{th}$ voxel (j=1 . . . J), T(x) is a warping function from frame n to frame m, and M is the total number of frames in the first plurality of frames and the second plurality of frames.

7. The method of claim 1, wherein the first modality data comprises one of magnetic resonance imaging modality data or computed tomography modality data.

8. The method of claim 7, wherein the first set of first modality data comprises a field of view greater than a field of view of the first set of second modality data.

9. The method of claim 7, wherein the second modality data comprises positron emission tomography modality data.

10. A non-transitory, computer readable medium storing computer executable instructions which cause a computer to execute the steps of:
generating a first set of first modality data including a first mu-map, a plurality of gated data, and a plurality of motion vectors, wherein the first set of first modality data is generated by a first imaging modality of an imaging system;
generating a first plurality of attenuation maps from the first set of first modality data, wherein each of the first plurality of attenuation maps corresponds to a gate in the first plurality of gated data;
generating a first set of second modality data including a first plurality of frames, wherein each of the plurality of frames corresponds to one of the plurality of attenuation correction maps, and wherein the first set of second modality data is generated by a second imaging modality of the imaging system;
warping the first plurality of frames by one or more corresponding motion vectors from the plurality of motion vectors and a corresponding attenuation map from the plurality of attenuation maps;
generating a first single-bed image by combining the first plurality of warped frames
generating a second set of first modality data including a second mu-map, a second plurality of motion vectors, and a second plurality of gated data;
generating a second plurality of attenuation maps from the second set of first modality data, wherein each of the second plurality of attenuation maps corresponds to a gate in the second plurality of gated data;
generating a second set of second modality data including a second plurality of frames, wherein each of the second plurality of frames corresponds to one of the second plurality of attenuation correction maps;
warping the second plurality of frames by one or more corresponding motion vectors from the plurality of motion vectors and a corresponding attenuation map from the plurality of attenuation maps;
generating a second single-bed image by combining the second plurality of warped frames; and
generating a whole body image by combining the first single-bed image and the second single-bed image.

11. The non-transitory, computer readable medium of claim 10, wherein generating each of the first and second single-bed images comprises applying a motion compensated sensitivity term and summing the respective plurality of image frames.

12. The non-transitory, computer readable medium of claim 11, wherein generating the whole body image comprises summing each of the single-bed images.

13. The non-transitory, computer readable medium of claim 12, wherein the whole body image is generated according to the equation:

$$f^{prmc}(\overline{x}) = \frac{\sum_{b=1}^{B}\sum_{n=1}^{M}(T_{m,n,b}(\overline{x})(f_{n,b}(\overline{x}) \cdot r_{n,b}(\overline{x}) \cdot d_{n,b}(\overline{x})))}{\sum_{b=1}^{B}\sum_{n=1}^{M}((T_{m,n,b}(\overline{x})(r_{n,b}(\overline{x}) \cdot d_{n,b}(\overline{x}))))}$$

where $r(\overline{x})$ is the sensitivity weighting term, $d(\hat{x})$ is a frame duration, m is the number of image frame, $f(\overline{x})$ is a discretized version of frame m and bed b, $\overline{x}$ is a center of a $j^{th}$ voxel (j=1 . . . J), T(x) is a motion correction function, and M is the total number of frames in the first plurality of frames and the second plurality of frames.

14. The non-transitory, computer readable medium of claim 13, wherein the first imaging modality comprises one of a magnetic resonance imaging modality or a computed tomography modality.

15. The non-transitory, computer readable medium of claim 14, wherein the second imaging modality comprises a positron emission tomography modality.

16. A system for medical imaging, comprising:
a first imaging modality;
a second imaging modality; and
a computer in data communication with the first imaging modality and the second imaging modality, the computer configured to process data for medical imaging by:
generating a first set of first modality data including a first mu-map, a plurality of gated data, and a plurality of motion vectors, wherein the first set of first modality data is generated by a first imaging modality of an imaging system;
generating a first set of second modality data including a first plurality of frames, wherein each of the plurality of frames corresponds to one or more of the plurality of motion vectors, and wherein the first set of second modality data is generated by a second imaging modality of the imaging system;
warping the first plurality of frames by one or more corresponding motion vectors from the plurality of motion vectors; and generating a first single-bed image by combining the first plurality of warped frames generating a second set of first modality data including a second mu-map, a second plurality of motion vectors, and a second plurality of gated data;

generating a second plurality of attenuation maps from the second set of first modality data, wherein each of the second plurality of attenuation maps corresponds to a gate in the second plurality of gated data;

generating a second set of second modality data including a second plurality of frames, wherein each of the second plurality of frames corresponds to one of the second plurality of attenuation correction maps;

warping the second plurality of frames by one or more corresponding motion vectors from the plurality of motion vectors and a corresponding attenuation map from the plurality of attenuation maps;

generating a second single-bed image by combining the second plurality of warped frames; and generating a whole body image by combining the first single-bed image and the second single-bed image.

17. The system of claim 16, wherein the first imaging modality comprises one of a magnetic resonance imaging modality or a computed tomography modality and the second imaging modality comprises a positron emission topography modality.

* * * * *